(12) United States Patent
Marx et al.

(10) Patent No.: US 6,230,717 B1
(45) Date of Patent: May 15, 2001

(54) MOTORIZED DISPOSABLE TOOTHBRUSH

(75) Inventors: Alvin J. Marx, 511 Mirepoix, San Antonio, TX (US) 78232; Kenneth A. Tarlow, Conte Madera, CA (US)

(73) Assignee: Alvin J. Marx, San Antonio, TX (US)

( * ) Notice: Subject to any disclaimer, the term of this patent is extended or adjusted under 35 U.S.C. 154(b) by 0 days.

(21) Appl. No.: 09/430,647

(22) Filed: Oct. 29, 1999

Related U.S. Application Data

(63) Continuation-in-part of application No. 09/295,147, filed on Apr. 26, 1999.

(51) Int. Cl.$^7$ .................................................. A46B 13/02
(52) U.S. Cl. ........................................... 132/308; 15/167.1
(58) Field of Search ..................... 132/322, 308; 433/125, 133, 130; 15/167.1

(56) References Cited

U.S. PATENT DOCUMENTS

| | | |
|---|---|---|
| 3,468,306 | 9/1969 | Heitzman . |
| 3,472,045 * | 10/1969 | Nelsen et al. ......................... 433/125 |
| 3,568,667 | 3/1971 | Krieger . |
| 3,771,517 | 11/1973 | Radecki . |
| 3,822,432 * | 7/1974 | Skinner ................................. 433/125 |
| 4,079,517 | 3/1978 | Zacharia . |
| 4,201,200 | 5/1980 | Hüber . |
| 4,371,341 | 2/1983 | Nakanishi . |
| 4,595,365 | 6/1986 | Edel . |
| 4,827,552 * | 5/1989 | Bojar et al. .......................... 15/167.1 |
| 4,989,287 | 2/1991 | Scherer . |
| 5,000,684 * | 3/1991 | Odrich ................................. 433/125 |
| 5,013,241 | 5/1991 | von Gutfeld . |
| 5,071,348 * | 12/1991 | Woog .................................... 132/308 |
| 5,072,477 | 12/1991 | Pai . |
| 5,082,444 | 1/1992 | Rhoades . |
| 5,099,536 * | 3/1992 | Hirabayashi ......................... 433/125 |
| 5,416,942 | 5/1995 | Baldacci . |
| 5,499,422 | 3/1996 | Lavazoli . |
| 5,529,495 * | 6/1996 | Edwards .............................. 433/125 |
| 5,613,258 * | 3/1997 | Hillfinger et al. .................. 15/167.1 |
| 5,699,575 | 12/1997 | Peifer . |
| 5,772,616 | 6/1998 | Competiello . |
| 5,902,107 * | 5/1999 | Lowell ................................. 433/125 |

* cited by examiner

*Primary Examiner*—Todd E. Manahan
(74) *Attorney, Agent, or Firm*—Grant E. Pollack; Nixon Peabody LLP

(57) ABSTRACT

A motorized, disposable toothbrush and method of using the same, the toothbrush including a housing with a handle portion, a neck portion and a head portion. At least one of the portions is constructed of a polymeric material. A brush head is rotatably mounted to the head portion, a variable, high speed motor being provided for effecting rotation of the brush head. The neck portion has a bend for orienting the brush head generally at a right angle for engagement of a user's teeth. A worm gear and flex joint assembly couples the motor to the brush head for effecting rotation thereof. A lithium based DC power source is provided for operation of the motor, power control being effected by a variable speed power control device which actuates rotation of the brush head in at least two power settings.

27 Claims, 10 Drawing Sheets

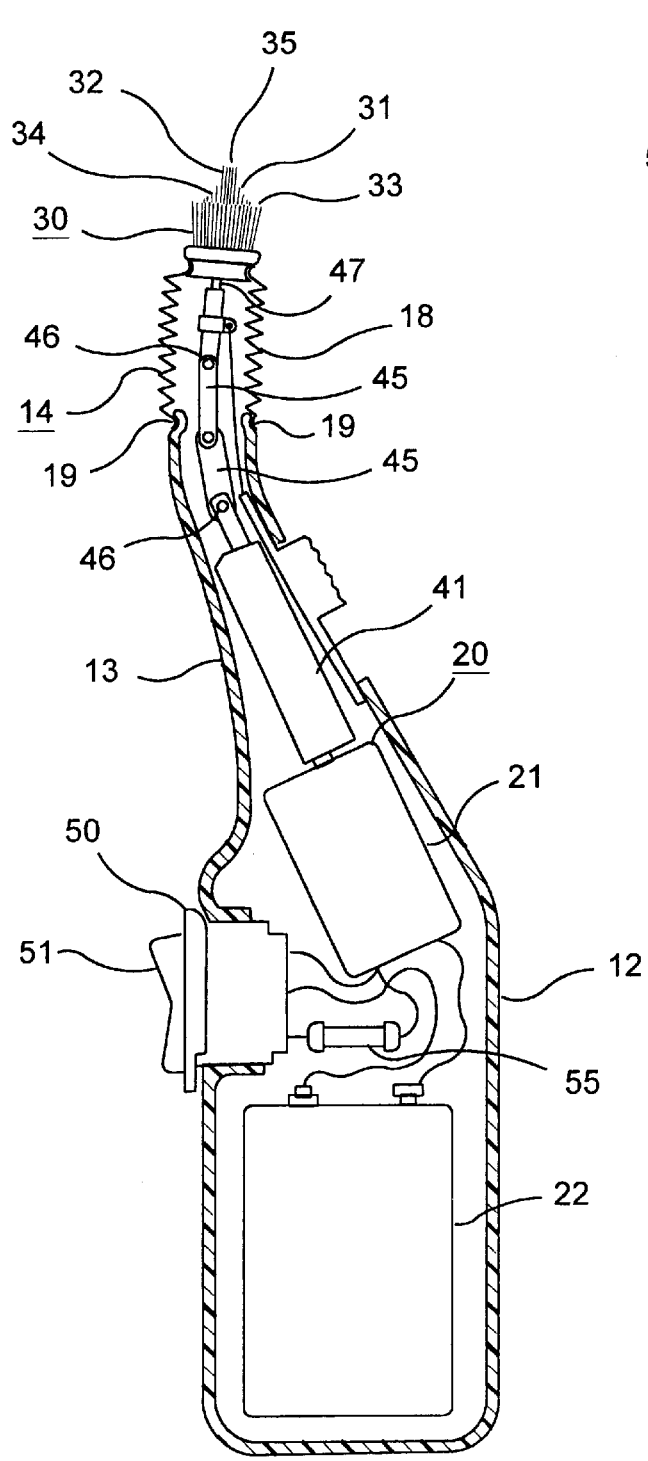
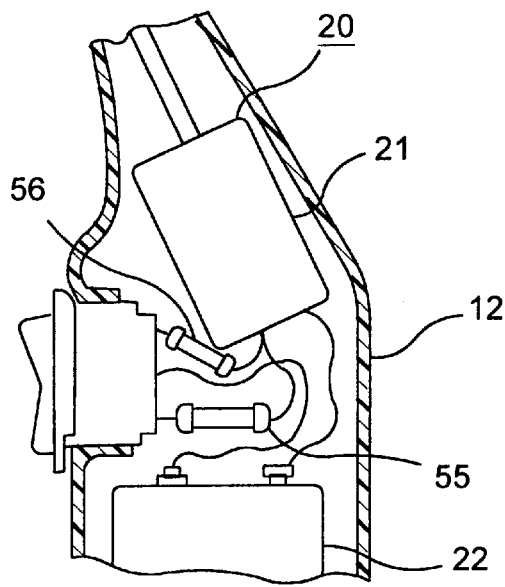
FIG. 4A
FIG. 4

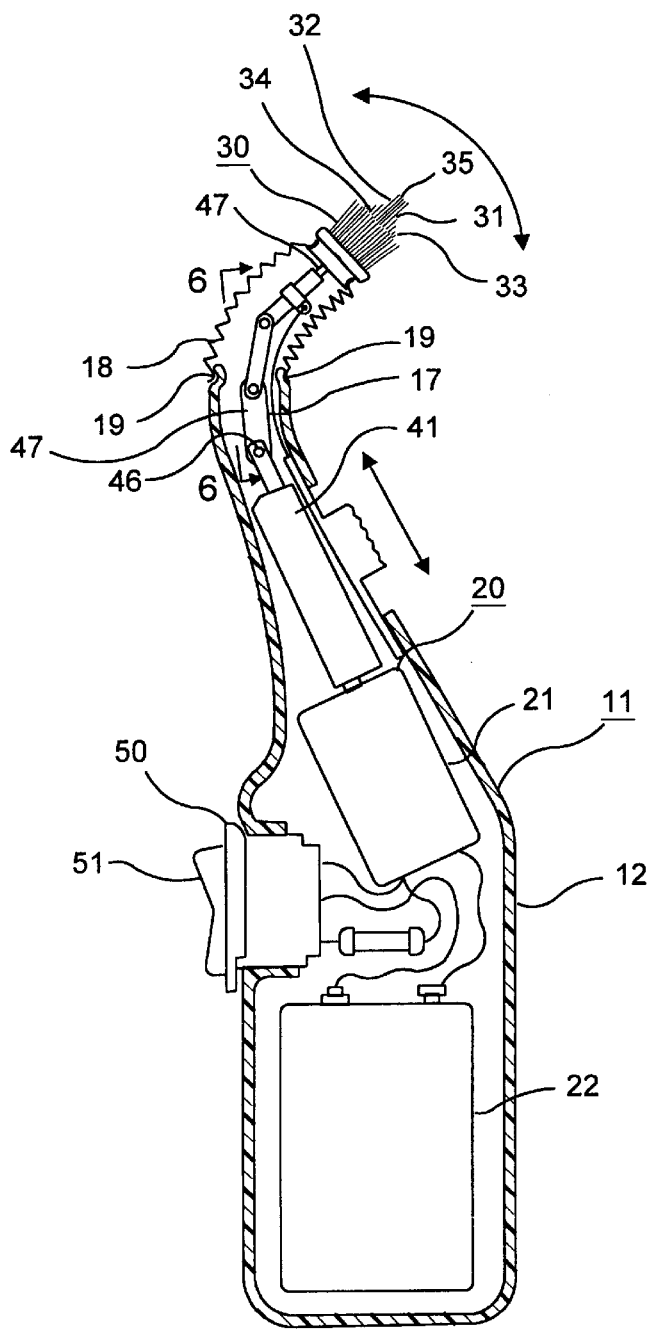
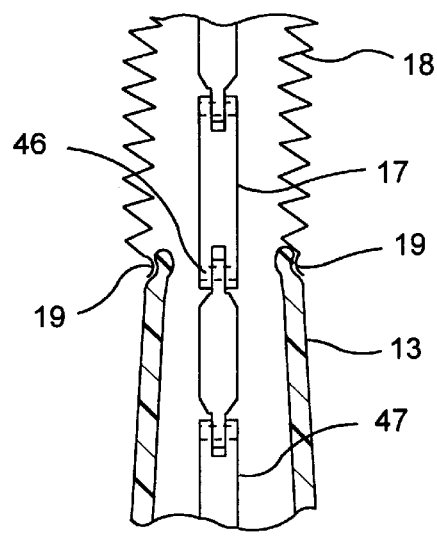
FIG. 5
FIG. 6

MOTORIZED DISPOSABLE TOOTHBRUSH

This application is a continuation-in-part of co-pending applicaion Ser. No. 09/295,147, filed Apr. 26, 1999, entitled "Novel Formulations of Magnesium Compounds For Local Application".

BACKGROUND OF THE INVENTION

The present invention relates generally to oral hygiene and more particularly to an improved device for cleaning teeth, gums and the like.

Conventional devices for oral cleansing have ranged from the traditional manual toothbrush to electronic devices. For instance, electric toothbrushes such as those with axial and lateral oscillating brushes have been used to simulate the up and down, back and forth strokes of a manual toothbrush. These devices are typically powered by rechargeable, though somewhat short-lived, battery packs and/or tethered electrical cords. While useful for removing debris from the sides of the teeth, they have been found less effective between teeth, under the gums, and around irregularly shaped teeth. User skill and flossing therefore remain essential for optimum oral hygiene. Moreover, their relative weight, cost, degree of reliability and safety considerations have made these conventional devices considerably less successful than the manual toothbrush.

Pressurized water jets have also been used as an alternative to the manual toothbrush. Typically, a probe is provided that emits a stream of water under relatively high pressure, the probe being connected to a water storage cell or reservoir. Although generally effective, the velocity of water necessary for effective cleaning has also been found to damage gums and other oral tissues. Lower velocity water containing abrasives, plaque dissolving compounds or the like have also been utilized, though with increased cost and decreased practicality. Water probes have, in addition, been plagued with all of the drawbacks associated with electric toothbrushes.

Another method that has been found useful for cleaning teeth is the use of ultrasonics. In particular, an ultrasonic, wave emitting wand or probe is inserted in the user's mouth and rubbed gently against areas of the teeth to be cleaned. The ultrasonic waves cause the debris to break down and dislodge from tooth surfaces, allowing it to be readily rinsed from the user's mouth. While highly effective as compared to the other teeth cleaning methods, their expense, practicality and reliance on the skill of the user have hindered growth in its use. In addition, the long term effects of ultrasonics on tooth enamel and gums are generally unknown and are a concern to some users.

Despite the many technological advances in electronic teeth cleaning apparatus, the old fashioned, manual toothbrush remains the most popular method for cleaning teeth. This is believed due not only to its simplicity, practicality, disposability and cost, but also its many design innovations ranging from new bristle materials and patterns, to angled brush heads and contoured brush handles. Its effectiveness, however, still depends in large part, on the skill and vigilance of the user. Steadily increasing costs have lead most users to use the same toothbrush well beyond its intended design life. The resulting worn brush with characteristic bowed bristles is not only unsanitary, but also has significantly reduced debris removal capability, particularly for removal between teeth and below the gums.

A toothbrush is therefore desired which not only provides superior cleaning of teeth and gums with minimal effort of the user, but is also safe, practical, convenient and inexpensive.

SUMMARY OF THE INVENTION

In accordance with one aspect of the present invention is a motorized toothbrush which comprises a housing with a handle portion, a neck portion and a head portion, at least one of the portions being constructed of a polymeric material. A brush head is rotatably mounted to the head portion, a variable, high speed motor being provided for effecting rotation of the brush head. The neck portion includes a bend for orienting the brush head generally at right angles to the handle portion for selected engagement of a user's teeth. A worm gear and flex joint assembly is provided for coupling the motor to the brush head and effecting rotation thereof. The motor is powered by a lithium-based DC power source. Rotation of the brush head is actuated in at least two power settings using a variable speed power control device.

According to another aspect of the present invention is a motorized toothbrush which comprises a housing with a handle portion, a neck portion and a head portion, at least one of the portions being constructed of a polymeric material. A concave profiled brush head is rotatably mounted to the head portion, a variable, high speed motor being provided for effecting rotation of the brush head. The neck portion has a bend for orienting the brush head generally at a right angle to the handle portion for selected engagement of a user's teeth. A worm gear and flex joint assembly is provided for coupling the motor to the brush head and effecting rotation thereof. The motor is powered by a lithium-based DC power source. Rotation of the brush head is actuated in at least two power settings using a variable speed power control device. The device includes an adjustable gear reducer for effecting first and second brush head speeds, respectively.

In accordance with a further aspect of the present invention is a method of cleaning a user's teeth using a motorized toothbrush, which comprises the steps of:

(i) inserting a head portion of the toothbrush in the user's mouth, the toothbrush comprising a housing with the head portion, a handle portion and a neck portion, at least one of the portions being constructed of a polymeric material, a brush head being rotatably mounted to the head portion, and the neck portion having a bend for orienting the brush head generally at a right angle to the handle portion for selected engagement of a user's teeth;

(ii) engaging a high speed motor in the handle portion for effecting rotation of the brush head at a selected speed, a worm gear and flex joint assembly coupling the motor to the brush head for effecting rotation thereof, and a lithium-based DC power source for operating the motor, engagement being effected using a variable speed power control device for actuating rotation of the brush head in at least two power settings;

(iii) placing the rotating brush head in contact with at least one of the user's teeth for a selected time;

(iv) removing the head portion from the user's mouth; and (v) disengaging the high speed motor.

In accordance with yet another aspect of the present invention is a method of cleaning a user's teeth using a motorized toothbrush which includes a housing with a head portion, a handle portion and a neck portion, the method comprising the steps of:

(i) engaging a high speed motor in a handle portion of the toothbrush for effecting rotation of a brush head in the head portion of the toothbrush at a selected speed, at least one of the portions being constructed of a polymeric material, a worm gear and flex joint assembly coupling the motor to the brush head for effecting rotation thereof; and a lithium-based DC power source for operating the motor, engagement being effected using a variable speed power control device for actuating rotation of the brush head in at least two power settings;

(ii) inserting the head portion of the toothbrush in the user's mouth, a brush head being rotatably mounted to the head portion, and the neck portion having a bend for orienting the brush head generally at a right angle to the handle portion for selected engagement of a user's teeth;

(iii) placing the rotating brush head in contact with at least one of the user's teeth for a selected time;

(iv) disengaging the high speed motor; and (v) removing the brush head from the user's mouth.

According to still another aspect of the present invention, there is provided, in combination, a motorized toothbrush and stand. The toothbrush comprises a housing with a handle portion, a neck portion and a head portion, at least one of the portions being constructed of a polymeric material. A brush head is rotatably mounted to the head portion, a variable, high speed motor being provided for effecting rotation of the head. The neck portion has a bend for orienting the brush head generally at a right angle to the handle portion for selected engagement of a user's teeth. A worm gear and flex joint assembly is provided for coupling the motor to the brush head and effecting rotation thereof. The motor is powered by a lithium-based DC power source. Rotation of the brush head is actuated in at least two power settings using a variable speed power control device. Finally, a support structure is utilized for suspending the toothbrush in a generally upright position.

In accordance with yet a further aspect of the present invention is a motorized toothbrush assembly which comprises a brush head rotatably mounted to the head portion, a variable, high speed motor for effecting rotation of the brush head, a lithium-based DC power source for operation of the motor, and a variable speed power control device for actuating rotation of the brush head.

In accordance with another aspect of the present invention is a motorized toothbrush assembly which comprises a brush head rotatably and detachably mounted to the head portion, a variable, high speed motor for effecting rotation of the brush head, a lithium-based DC power source for operation of the motor, and a variable speed power control device for actuating rotation of the brush head.

Accordingly, it is an object of the present invention to provide an improved disposable device for oral hygiene.

Another object of the present invention is to provide an electric toothbrush having a non-rechargeable, leak proof battery which has a design life at least as long as that of the toothbrush bristles.

A further object of the present invention is to provide a practical, light weight electric toothbrush that is safe, durable and reliable.

Yet another object of the present invention is to provide an improved electric toothbrush that readily fits the contour of a user's hand.

Still another object of the present invention is to provide an electric toothbrush which effectively cleans virtually any interior portion of a user's mouth with minimal skill and vigilance of the user.

Yet a further object of the present invention is to provide an improved electric toothbrush which is constructed of low cost materials.

Another object of the present invention is to provide an improved oral hygiene device which utilizes no chemical additives.

A further object of the present invention is to provide an improved electric toothbrush that is easy to store for travel and requires no recharging or battery replacement.

Still another object of the present invention is to provide an improved device and method of cleaning teeth, gums and the like.

Yet another object of the present invention is to provide an electric toothbrush that is both practical and economical.

The present invention will now be further described by reference to the following drawings which are not intended to limit the accompanying claims.

BRIEF DESCRIPTION OF THE DRAWINGS

FIG. 4 is a cut-away plan view of a motorized, disposable toothbrush, in a first operative position, according to a further aspect of the present invention;

FIG. 4A is a cut-away plan view of a motorized, disposable toothbrush, in accordance with still another aspect of the present invention;

FIG. 5 is a cut-away plan view of the toothbrush set forth in FIG. 4 showing the toothbrush in a second operative position and the range of motion of the adjustable neck portion;

FIG. 6 is a sectional view taken along line 5—5 of FIG. 5 showing a flex joint in accordance with the present invention;

The same numerals are used throughout the figure drawings to designate similar elements. Still other objects and advantages of the present invention will become apparent from the following description of the preferred embodiments.

DETAILED DESCRIPTION OF THE PREFERRED EMBODIMENTS

Figures 1, 1A:
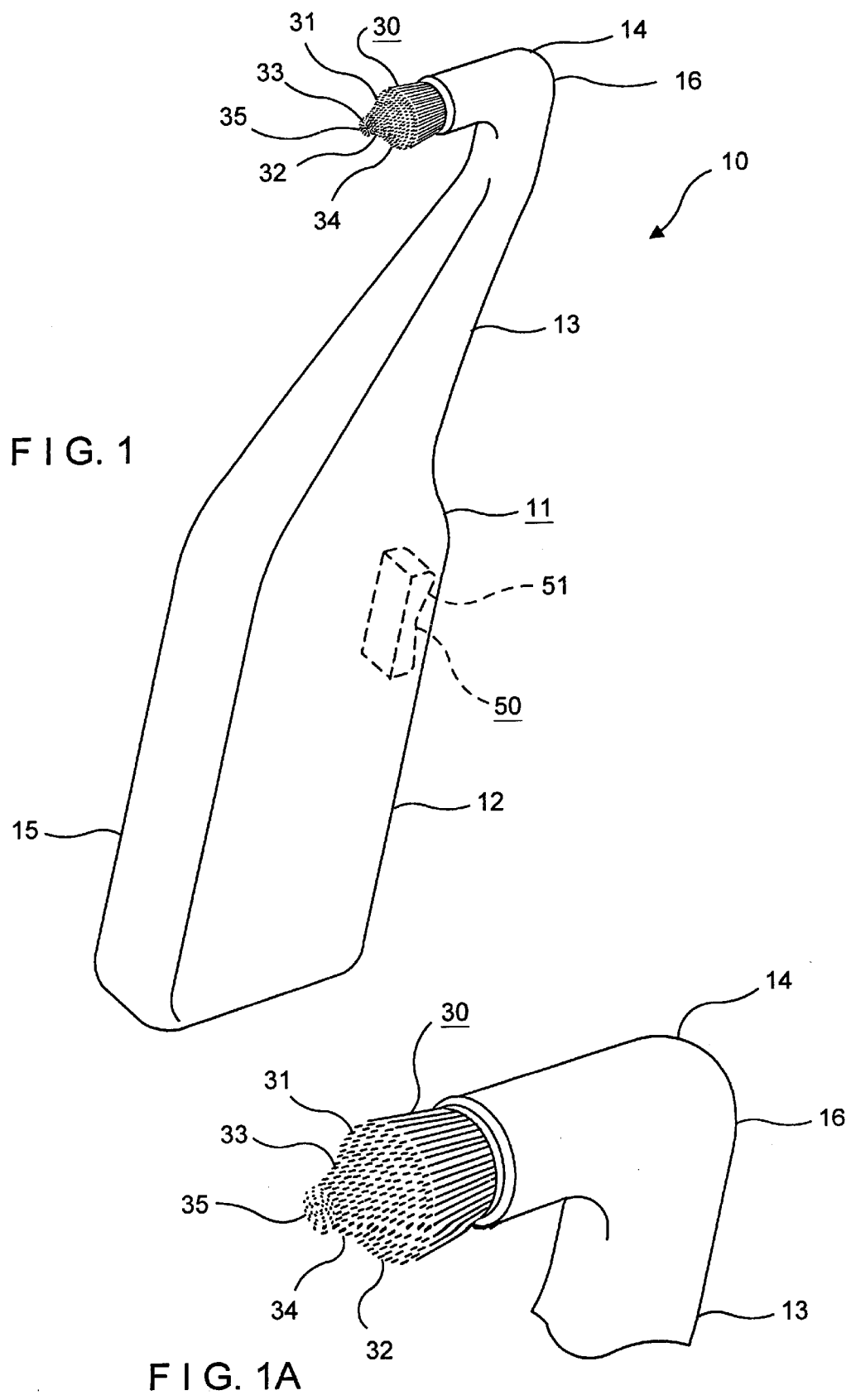
FIG. 1 is a perspective view of a motorized, disposable toothbrush, according to one aspect of the present invention.
FIG. 1A is a cut-away perspective view of the brush head and neck portion shown in FIG. 1.
Figure 2:
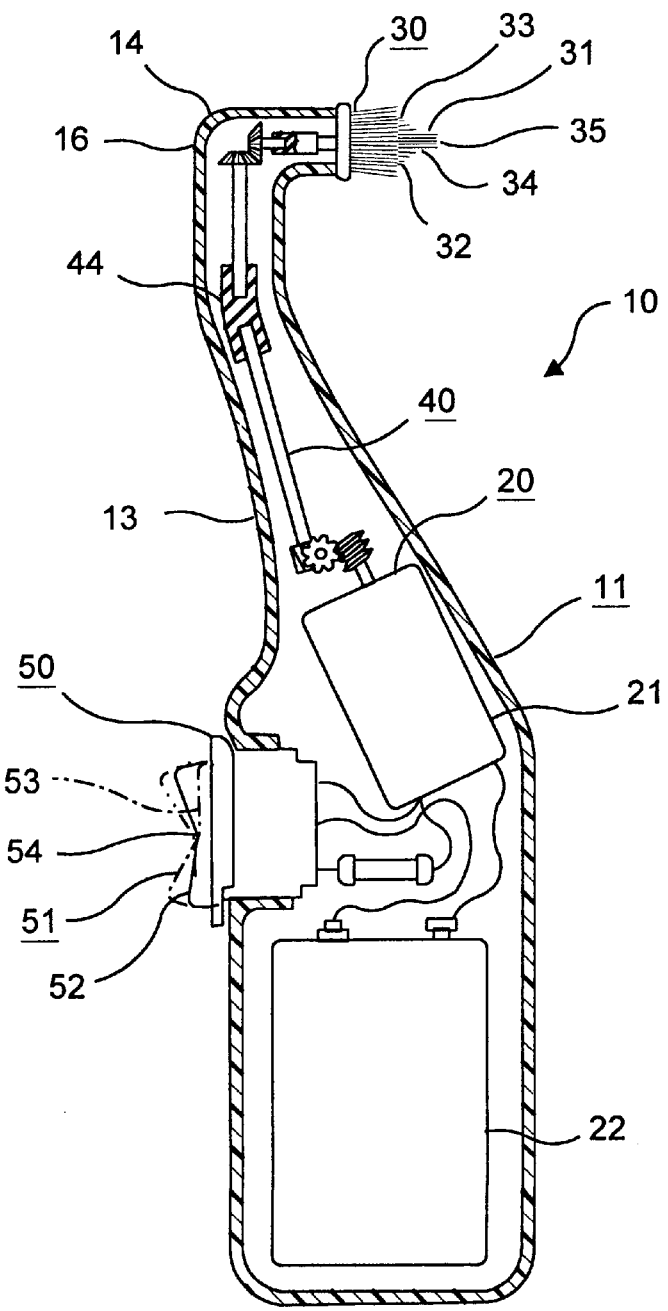
FIG. 2 is a cut-away plan view of the toothbrush set forth in FIG. 1.

Referring now to the drawings and more particularly to FIGS. 1–13, there is shown generally a specific, illustrative, motorized disposable toothbrush 10 according to various aspects of the present invention. As shown in FIG. 1, the toothbrush has a housing 11 with a handle portion 12, a neck portion 13 and a head portion 14. A variable, high speed motor 20 is provided for effecting rotation of a brush head 30 rotatably mounted to the head portion. As shown in FIG. 2, a worm gear and flex joint assembly 40 is provided for coupling the motor to the brush head and for effecting rotation thereof. Rotation of the brush head is actuated in at least two power settings using a variable speed power control device 50.

It is preferred that the housing be a one piece unit 15, effectively sealed from the ingress (or egress) of fluids such as water or air. A one piece construction is advantageous in allowing relatively simple, inexpensive manufacture with an airtight, waterproof seal that prolongs toothbrush life. Specifically, this seal not only protects the battery and working mechanisms from moisture, thereby improving reliability, but also enhances safety and prevents battery leakage outward from the unit. Each portion of the unit is preferably constructed of a polymeric material such as polyethylene, e.g., HID 112 manufactured by Chevron Corporation. Alternatively or concurrently therewith, a shell construction of a conventional high-impact resistant plastic is also desirable for minimizing risk of damage during travel.

Figure 3:
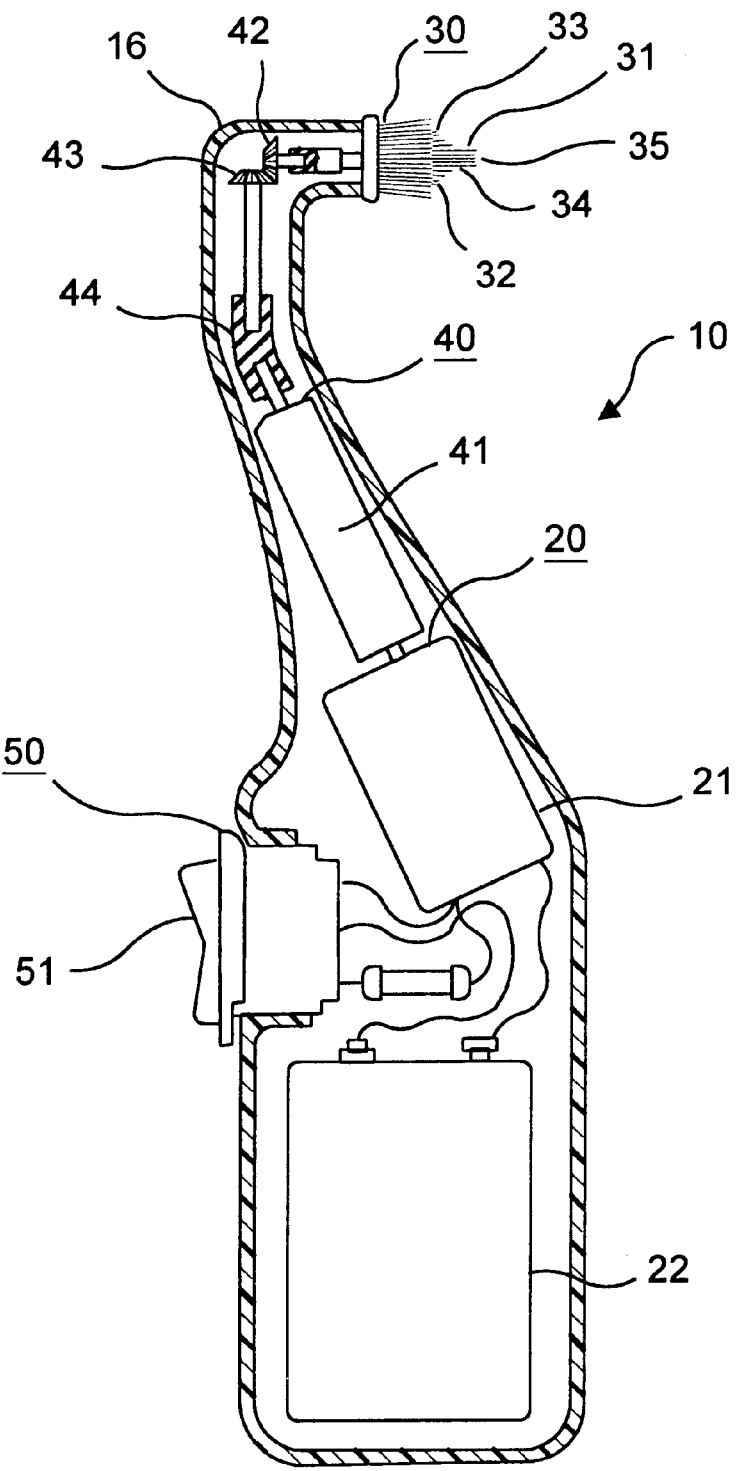
FIG. 3 is a cut-away plan view of a motorized, disposable toothbrush in accordance with another aspect of the present invention.
Figure 7:
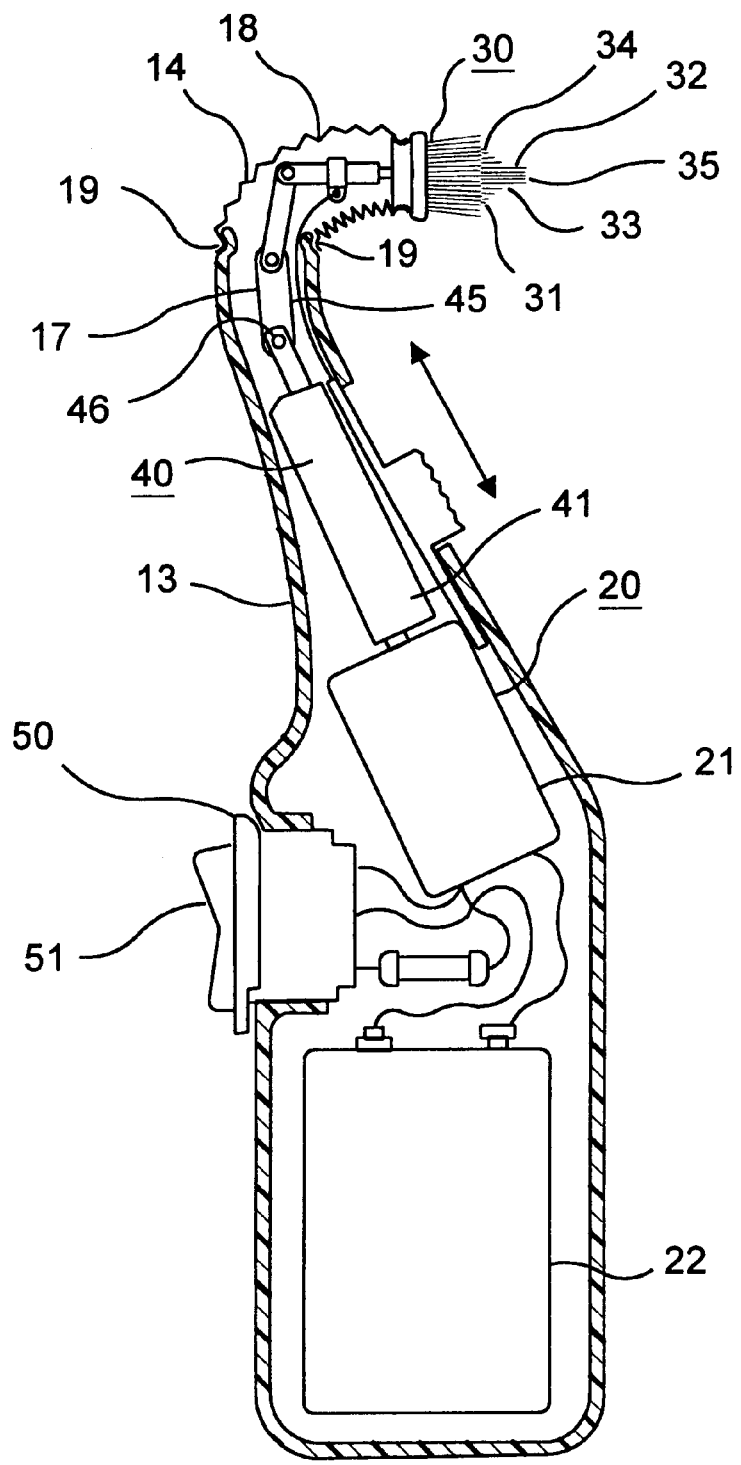
FIG. 7 is a cut-away plan view of the toothbrush set forth in FIG. 4 showing the toothbrush in a third operative position.

Rotation of brush head 30 is controlled by variable, high speed motor 20 housed suitably in the handle portion for effecting rotation thereof. In accordance with one aspect of the present invention, the brush head is provided with soft, compact nylon bristles 31 formed in a generally cone-like shape, best seen in FIG. 1A. The sides 32, 33 of the cone have a concave profile 34 and the top 35 is flattened, as illustrated in FIGS. 2 and 3. This configuration has not only been found highly effective for removing debris from between teeth, but also in cleaning between teeth and gums, rapid cleaning of the crown, as well as use on irregularly shaped teeth.

Figure 1B:
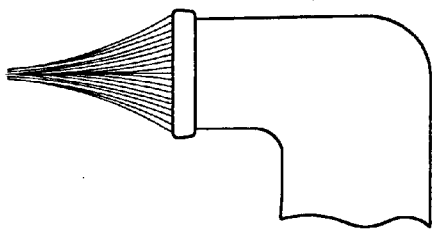
FIG. 1B is a perspective view of a brush head and neck portion according to another aspect of the present invention.

In an alternative embodiment, as shown in FIG. 1B, the brush head has a flattened shape. This arrangement has been found desirable for debris removal, polishing and gum messaging. In another embodiment, alternatively or concurrently with either of the foregoing brush head configurations, the brush head is detachably secured to the head portion such as by a snap fit for ready removal or replacement.

As indicated in FIGS. 1–3, neck portion 13 is generally fixed at a selected bend 16 for orienting the brush head generally at a hook-like or right angle. This provides ready positioning of the brush head over the user's lip and into generally perpendicular engagement with the user's teeth. The worm gear and flex joint assembly facilitates this effect.

Alternatively, the neck portion is adjustably flexible, in whole or in part, for variable positioning of the brush head in a selected orientation relative to the handle portion. A toothbrush of this general configuration is illustrated in FIGS. 4–7. Selected adjustment is preferably facilitated by a universal joint and bearing assembly 17 interior to the neck portion and a flex cord 18 comprising the exterior neck portion. The flex cord fits over a coupling lip 19 at the neck mid section for water tight securement therewith.

In this manner, a proper angle of the brush head relative to the teeth may be maintained for effective brushing. A flexible, bendable neck portion is also advantageous for placing the toothbrush in a stowed or folded position for storage, enhanced portability or the like.

As shown in FIGS. 2–7, motor 20 is preferably a conventional, low current DC motor 21 with a capacity of at least three (3) volts, powered by a selected DC power source 22 or the like. An objective is to provide selected constant, high speed rotation with minimal slow down upon contact with the teeth or gums. Suitability of other relatively low current motors will be appreciated by those skilled in the art, giving consideration to the purpose for which the present invention is intended.

Power source 22 is preferably lithium-based, e.g., a lithium manganese dioxide battery or the like, which is non-rechargeable, disposable, leak-proof and has a relatively long life. In this connection, a battery life of up to about six (6) months is achieved with normal use of the present invention, e.g., two times a day. Battery shelf life is preferably up to about 6 years. According to one aspect of the present invention, a single nine (9) volt lithium-based battery, e.g., lithium alkaline, is provided to operate the motor for extended normal use. Alternatively, the motor is powered by a three (3) volt power source comprising two (2) 1.5 volt lithium-based batteries. The foregoing arrangements are considered beneficial as power cords, adapters and the like are virtually eliminated.

Although the present invention has been shown and described in connection with a lithium-based DC power source, it will be understood by those skilled in the art that other suitable power sources may be utilized giving consideration to the purpose for which the present invention is intended.

Turning now to internal mechanisms according to the present invention, worm gear and flex joint assembly 40, which couples the motor to the brush head, permits translation of rotational motion from motor 20 to corresponding rotational motion of brush head 30. As will also be understood by those skilled in the art, a gear reducer 41 s preferred for this arrangement not only for facilitating the mechanical conversion, but also for minimizing power requirements vis-à-vis relatively high torque and low gear ratios. The gear reducer is best seen in FIGS. 3–7.

Figure 8:
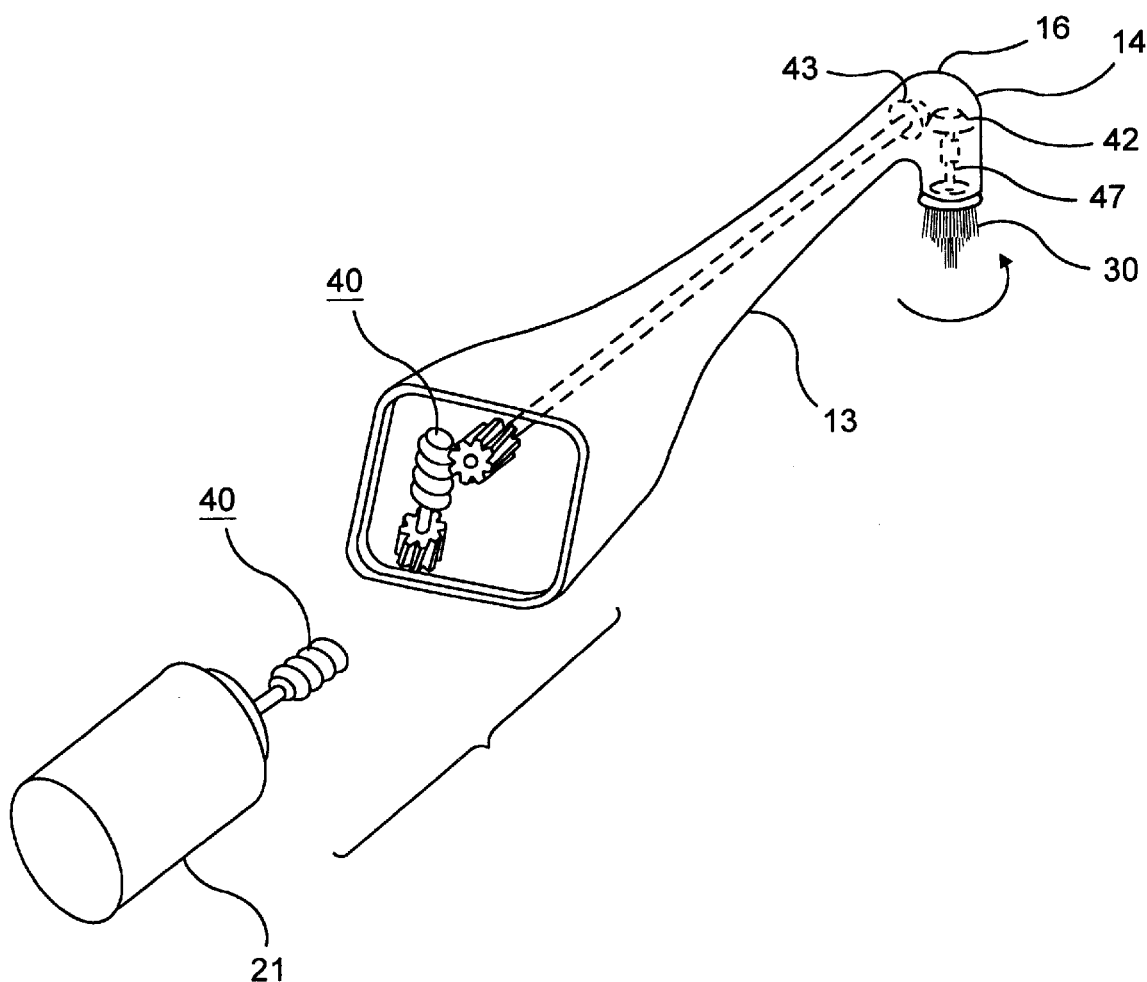
FIG. 8 is an exploded, partial perspective view of a motorized, disposable toothbrush according to another aspect of the present invention.
Figure 9:
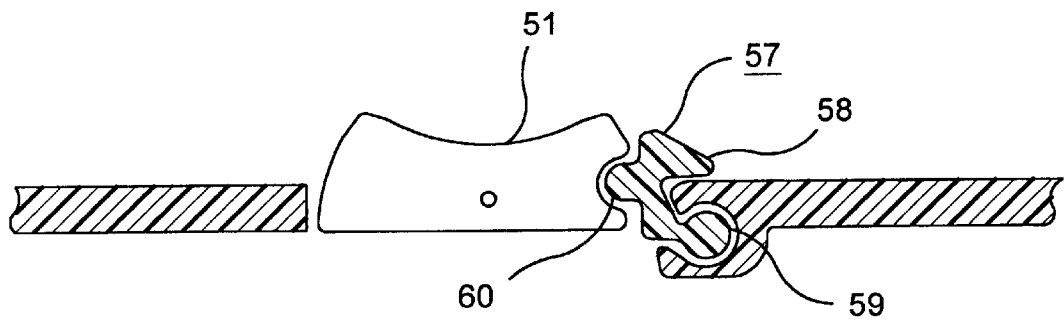
FIG. 9 is a sectional view of a locking power switch for the toothbrush set forth in FIG. 4, in the locked position.
Figure 10:
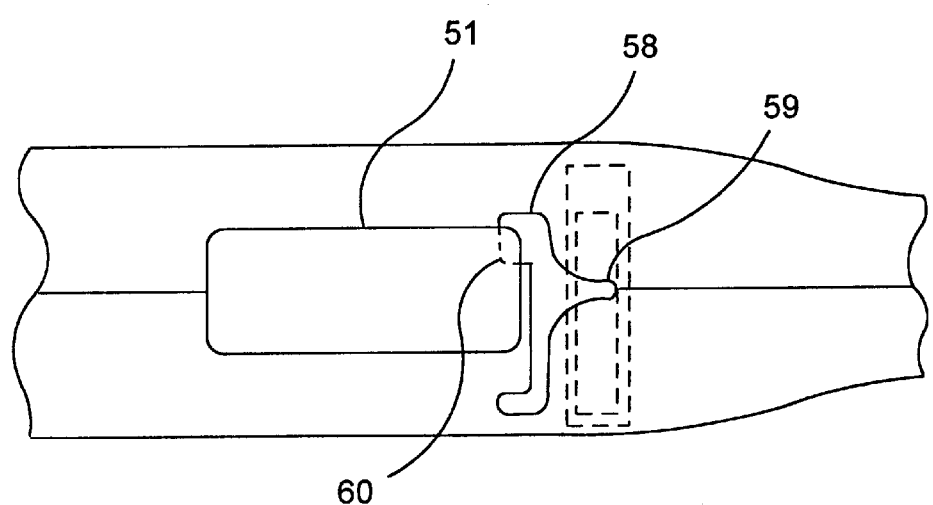
FIG. 10 is a plan view of the switch set forth in FIG. 9.
Figure 11:
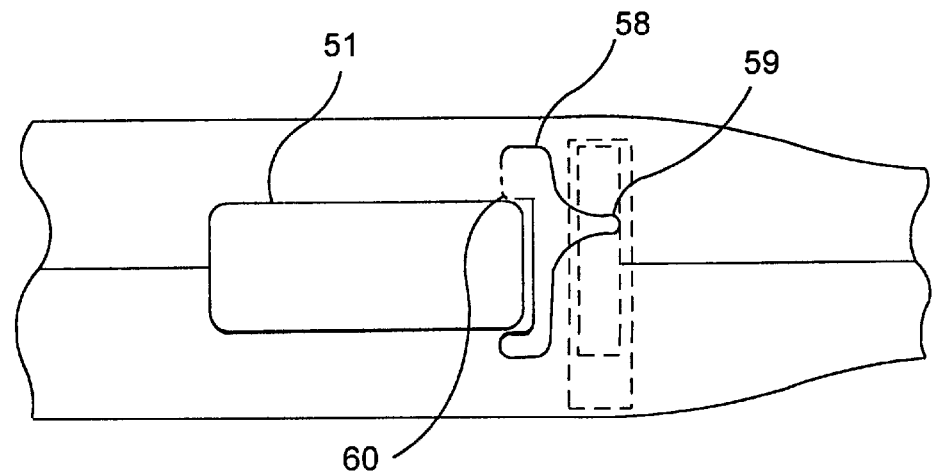
FIG. 11 is a plan view of the switch set forth in FIG. 9 in the unlocked position.

In the fixed neck embodiment, shown generally in FIGS. 2 and 3, the worm gear and flex joint assembly includes a gear reducer 41, a flex joint 44 and gears 42, 43 in the neck portion. The flex joint provides an operative bridge between the axle of gear reducer 41 and gear 43 for highly efficient transfer of axial motion to the brush head. Gears 42 and 43 are preferably mitered for effective, variable angle engagement. Alternatively, as illustrated in FIG. 8, a relatively straight neck portion is utilized whereby the flex joint is omitted.

According to one aspect of the invention, the gears are suitably constructed of an acetal resin such as Delrin® manufactured by Dupont de Nemours & Company. An objective is to provide a relatively quiet, inexpensive gear drive with enhanced durability and performance.

In the flexible neck embodiment, set forth in FIGS. 3–7, gear reducer 41 is linked to an axle 47 of the rotating brush head by universal joint and bearing assembly 17. The assembly comprises, for instance, a series of segmented coupler members 45 pivotally connected end to end at coupler joints 46. Other conventional worm gear and joint arrangements are considered suitable for this purpose, as will be appreciated by those skilled in the art.

Variable speed, power control device 50 for actuating rotation of the brush head is preferably a multi-position pivot switch 51 which may be actuated in at least two power settings. A three-position switch is used, according to one embodiment, the switch having a first position 52 corresponding to a first or LOW power setting, a second 53 corresponding to a second or HIGH power setting, and a third 54 to a power OFF position. Each power setting, in turn, corresponds to a selected brush head speed, for instance, the LOW power setting corresponding to a first brush head speed and the HIGH setting to a second brush head speed. Alternatively, a conventional sliding type multiposition switch may be used.

In one embodiment, gear reducer 41 is utilized for controlling rotation at the first head speed, e.g., about 450 RPM, at a first gear reducer setting having a relatively low gear ratio. To attain rotation at a second brush head speed such as about 600 RPM, a second gear reducer setting with corresponding higher gear ratio has been found desirable. Use of a resistor (not shown), alternatively or concurrently therewith, e.g., about 1 ohm, is also considered within the spirit and scope of the present invention. Low brush head speeds have been found suitable for cleaning near the gum line as having minimal abrasive effect upon the gums, whereas high brush head speeds are considered desirable for cleaning crowns of teeth where maximum abrasion is desired.

In another embodiment, set forth in FIG. 4A, a pair of resistors 55, 56 are provided in place of the gear reducer. Resistor 55, preferably about 1 ohm in magnitude, effects rotation at the first head speed, e.g., about 450 RPM. To attain rotation at the second brush head, e.g., 600 RPM, a resistor 56 of about ½ ohm has been found desirable.

Figure 13:
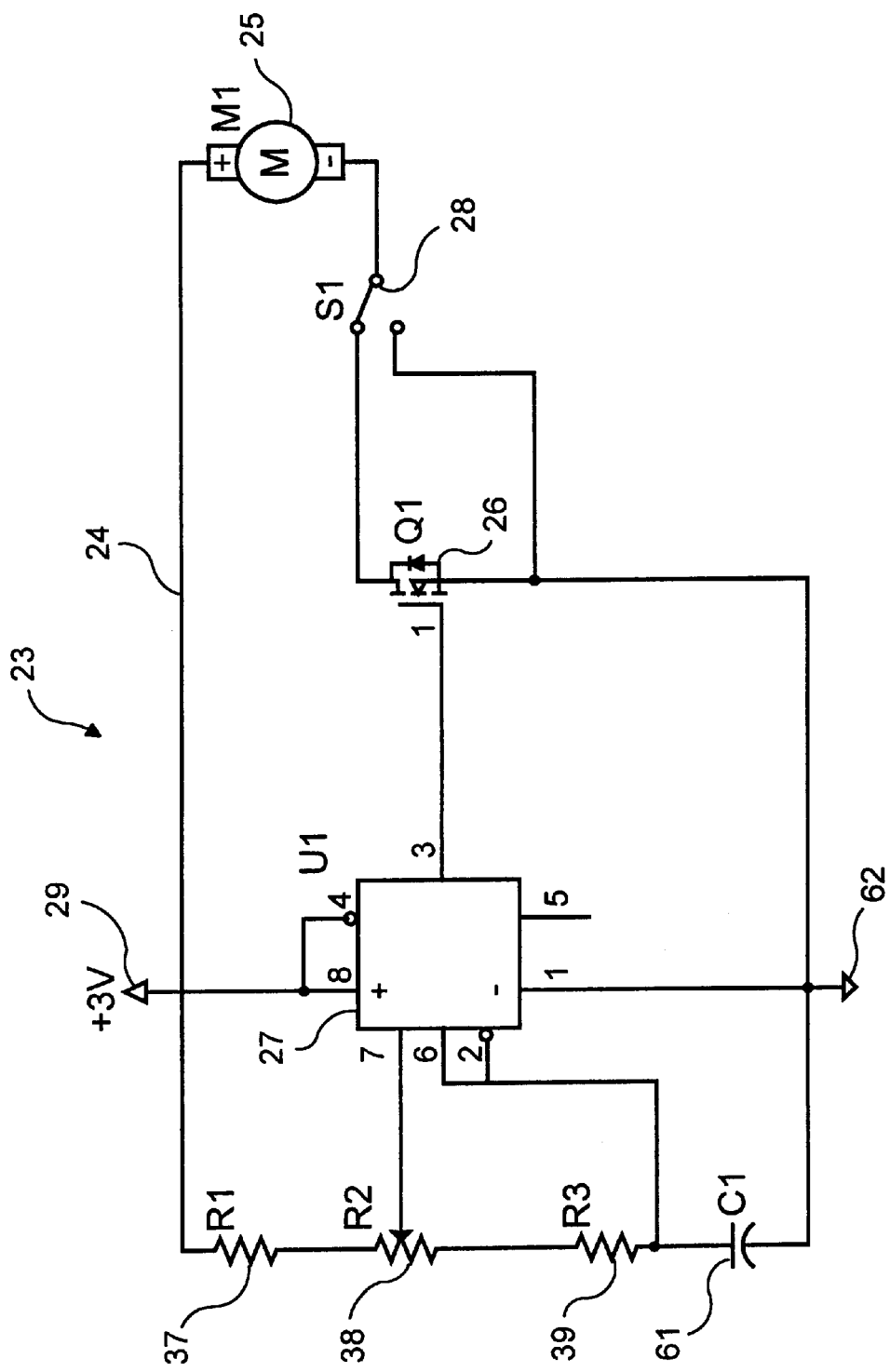
FIG. 13 is an electronic schematic showing a general purpose, low power rectifier according to the present invention.

Motor control may, in addition, be accomplished using a two speed, motor controller such as a conventional pulse width modulator 23. An electronic circuit 24 of this general description is illustrated in FIG. 13. The circuit includes a DC motor 25, MOSFET 26, a microprocessor or chip 27, e.g., part no. LM555CN, a two position switch 28 for selecting fast and slow speeds, a DC power source 29 such as two AA batteries, a series of resistors, 37, 38 and 39, a capacitor 61 and a ground 62. This circuit has been found particularly useful for reliable, precise, low energy speed control at a relatively low cost. A conventional diode, e.g., part no. 1N4001, is also suitable for this purpose as will be understood by those skilled in the art.

Generally speaking, bristle and brush head geometry as well as speed of rotation are considered relatively important for effective cleaning of teeth and gums, according to the various aspects of the present invention. For instance, in one embodiment, the tip of the brush head is less than about 1 cm in diameter. In particular, with reference to the formula, F (force)=m (mass)×a (acceleration), it has been determined that cleaning pressure is dependent on the force of friction and the area over which it is applied. This relationship, based upon F=ma, is illustrated by the following mathematical expression:

$$P_c = M_k N / A_c$$

Where $P_c$=the cleaning pressure or friction force, $M_k N$ is the force due to the kinetic friction of the moving brush, N is the normal force exerted by the tooth perpendicular to the tooth surface, and $A_c$ is the surface area being cleaned.

Since the dimensions of the tip are relatively small, its cone-shaped head allows more pressure, $P_c$, to be applied more uniformly to the tooth surface without damage to the gums. In addition, a small tip size allows the user to reach under or below the gum line, sparing the gum from lateral pressure. Moreover, the use of a rotating motion with a cone-shaped bristle increases the average speed of contact or friction between the bristles and the teeth as compared to conventional oscillating head toothbrushes. While this degree of friction is sufficient for debris removal, it has been found well below the threshold of abrasion to teeth or gums. Stated differently, this unique shape allows more pressure is applied to the surface of the teeth and less to the gums, particularly when applied to the based of the teeth, i.e., near the gingiva. Hence, the present invention provides an optimum combination of speed, bristle stiffness and geometry for maximum oral cleaning without damage to gums or the like.

Optimal use and comfort of the present invention is further facilitated by the uniquely shaped and sized handle portion 12. This feature not only fits the contour of a wide range of user hands, but also serves to guide the user to an appropriate grip and orientation for optimal use. Moreover, it provides a compact, practical geometry for greater versatility.

Figure 12:
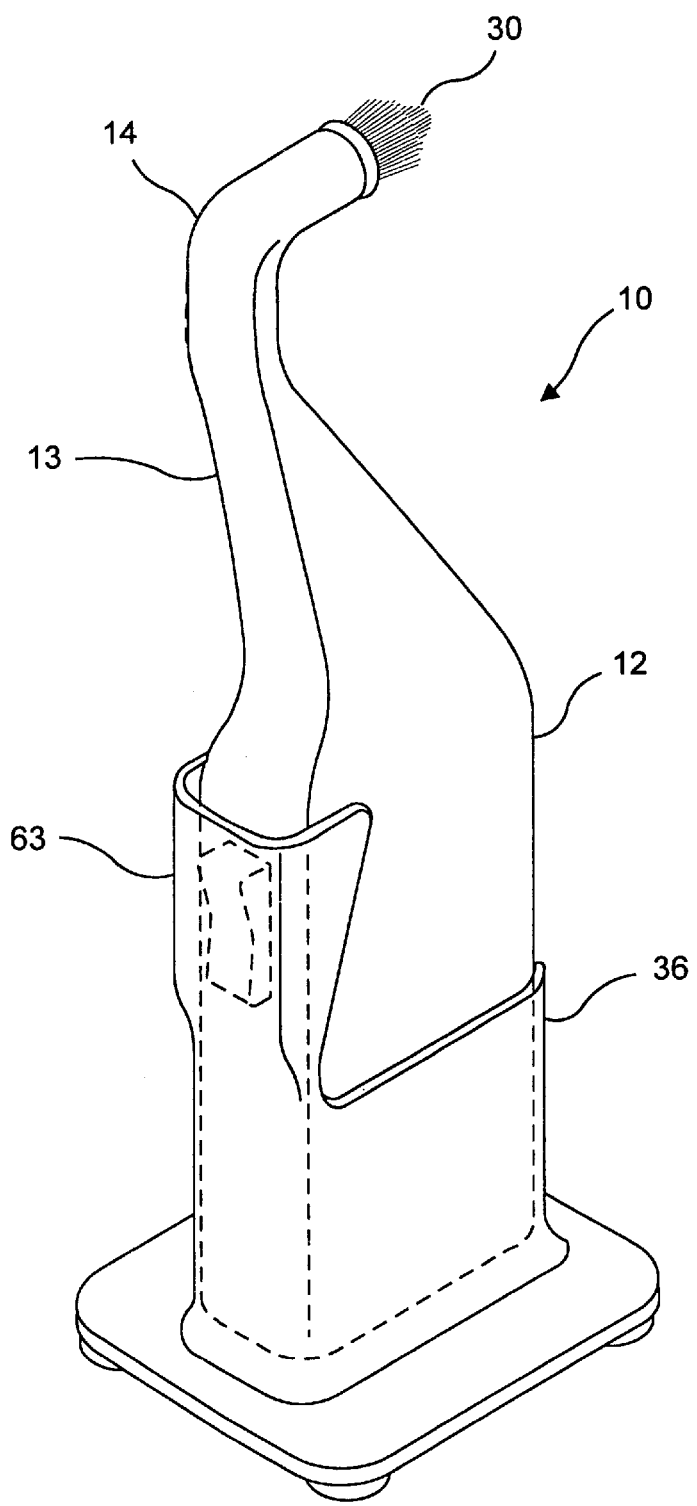
FIG. 12 is a perspective view of the toothbrush set forth in FIG. 1 mounted upright in a stand.

As illustrated in FIG. 12, a stand 36 may be provided for upright storage, protection and ready access to the motorized toothbrush. Upright storage is considered desirable not only for rapid drying of the brush head, but also minimizing accidental damage such as a user knocking or dropping the device onto hard surfaces such as a sink or bathroom floor. Alternatively or concurrently, the stand is equipped with a switch guard 63 to prevent the device from inadvertent engagement such as during travel in a suitcase and wearing out the battery.

A locking switch 57 is also desirable for use with the motorized toothbrush. A suitable locking mechanism, according to one embodiment, is set forth in FIGS. 9–11. The locking mechanism comprises a sliding latch 58 having dual opposing protrusions 59, 60, one for engaging a groove in the housing and the other mating with a corresponding groove of the power switch. As the switch is moved from a first or unlocked to a second or locked position, protrusion 60 enters the switch groove; sliding across the same and coming to rest in proximity to a center portion of the switch. To unlock the switch, latch 58 is moved generally in the opposite direction, protrusion 60 sliding back along the grove, until becoming disengaged therefrom. Upon disengagement, the switch is in the unlocked position.

Turning now to operation, a method is provided for cleaning a user's teeth using a motorized toothbrush. Initially, a head portion of the toothbrush is inserted in the user's mouth. Next, a speed setting is selected by the user, the motor in the handle portion being engaged thereby at a relatively high speed. Through the worm gear and flex joint assembly, rotation of the brush head is effected. The rotating brush head is then placed in contact with at least one of the user's teeth for a selected time. When a desired degree of cleaning has been achieved, the head portion is removed from the user's mouth, and the high speed motor is disengaged.

Alternatively, a speed setting is first selected by the user, the motor in the handle portion being engaged thereby at a relatively high speed. The head portion is then inserted in the user's mouth. Next, the rotating brush head is placed in contact with at least one of the user's teeth for a selected time. After a desired degree of cleaning has been achieved, the motor is disengaged. The head portion is then removed from the user's mouth.

In another alternative embodiment, a head portion of the toothbrush is initially inserted in the user's mouth. Next, the brush head is placed in contact with at least one of the user's teeth, and a speed setting is selected by the user, the motor in the handle portion being engaged thereby at a relatively high speed. After the rotating brush head has been in contact with at least one of the user's teeth for a selected time and a desired degree of cleaning has been achieved, the high speed motor is disengaged and the head portion is removed from the user's mouth. In still another alternative embodiment, the head portion is removed from the user's mouth and then the motor is disengaged.

The present invention, according to a further embodiment, has been found suitable for administering a dentifrice comprising selected compounds of magnesium or the like to the oral cavity, e.g., for treatment of periodontal disease. Compositions of this general description are set forth in U.S. Pat. No. 5,898,037 entitled "FORMULATIONS OF MAGNESIUM COMPOUNDS FOR LOCAL APPLICATION AND METHODS OF TREATMENT USING THE SAME," which issued to Alvin J. Marx on Apr. 27, 1999, the disclosure of which is hereby incorporated by reference in its entirety. Such compositions are administered desirably with the aid of vibration, such as that exhibited upon operation of the present invention. Effective vibration is preferably in the range of about 50 to about 1000 Hz (300–60,000 cycles per minute). For oral applications, the frequency of vibration of about 50 to about 100 Hz is preferred and more particularly, 80–85 Hz. For other topical applications, the frequency is preferably about 300 to about 700 Hz, and more preferably 400–600 Hz.

Overall, the present invention facilitates superior cleaning between teeth, under gums, and around braces without damage to the gums. The unit's relatively low cost makes it economically feasible as a relatively small, low cost, disposable consumer item, or as a low cost, reusable toothbrush with adaptation of a disposable brush head. Advantageously, wear of the brush head is correlated with battery life to minimize waste. Its durability, effectiveness and practicality are also considered unparalleled.

Various modifications and alterations to the present invention may be appreciated based on a review of this disclosure. These changes and additions are intended to be within the scope and spirit of this invention as defined by the following claims.

What is claimed is:

1. A motorized toothbrush comprising:
    a housing including a handle portion, a neck portion and a head portion, at least one of the portions being constructed of a polymeric material, the housing being a sealed one-piece unit;
    a brush head rotatably m ed to the head portion, the neck portion having a bend for orienting the brush head for engagement of a user's teeth generally at a right angle thereto;
    a variable, high speed motor for effecting rotation of the brush head, a worm gear and flex joint assembly coupling the motor to the brush head for effecting rotation thereof;
    a lithium based DC power source for operation of the motor; and
    a variable speed power control device for actuating rotation of the brush head in at least two power settings.

2. The motorized toothbrush set forth in claim 1 wherein the power control device includes a gear reducer for effecting a first brush head speed.

3. The motorized toothbrush set forth in claim 1 wherein the power control device includes a gear reducer for effecting a second brush head speed.

4. The motorized toothbrush set forth in claim 1 wherein the tip of the brush head is less than about 1 cm in diameter.

5. The motorized toothbrush set forth in claim 1 wherein the two power settings correspond to a first brush head speed and a second brush head speed.

6. The motorized toothbrush set forth in claim 1 wherein the power source is at least a 3 volt lithium alkaline battery.

7. The motorized toothbrush set forth in claim 1 wherein the brush head is cone-shaped.

8. The motorized toothbrush set forth in claim 1 wherein the brush head has a concave profile.

9. The motorized toothbrush set forth in claim 1 wherein the brush head is detachably secured to the head portion.

10. The motorized toothbrush set forth in claim 1 wherein the neck portion is adjustably flexible for positioning the brush head in a selected orientation relative to the handle portion.

11. The motorized toothbrush set forth in claim 1 wherein the handle portion is shaped and sized so as to fit the contour of a hand.

12. A motorized toothbrush comprising:
    a housing including a handle portion, a neck portion and a head portion, at least one of the portions being constructed of a polymeric material, the housing being a sealed one-piece unit;
    a concave profiled brush head rotatably mounted to the head portion, the neck portion having a bend for orienting the brush head for engagement of a user's teeth generally at a right angle thereto;
    a variable, high speed motor for effecting rotation of the brush head; a worm gear and flex joint assembly coupling the motor to the brush head for effecting rotation thereof,
    a lithium based DC power source for operation of the motor; and
    a variable speed power control device for actuation rotation of the brush head in at least two power settings, the power control device includes a variable gear reducer for effecting first and second brush head speeds.

13. The motorized toothbrush set forth in claim 12 wherein the tip of the brush head is less than about 1 cm in diameter.

14. The motorized toothbrush set forth in claim 12 wherein the power source is about a 9 volt lithium manganese dioxide battery.

15. The motorized toothbrush set forth in claim 12 wherein the brush head is detachably secured to the head portion.

16. The motorized toothbrush set forth in claim 12 wherein the neck portion is adjustably flexible for positioning the brush head in a selected orientation relative to the handle portion.

17. The motorized toothbrush set forth in claim 12 wherein the handle portion is shaped and sized so as to fit the contour of a hand.

18. A method of cleaning a user's teeth using a motorized toothbrush, which comprises the steps of:
    (i) inserting a head portion of the toothbrush in the user's mouth, the toothbrush comprising a housing including the head portion, a handle portion and a neck portion, at least one of the portions being constructed of a polymeric material, a brush head being rotatably mounted to the head portion, and the neck portion having a bend for orienting the brush head for engagement of a user's teeth generally at a right angle thereto, the housing being a sealed one-piece unit;
    (ii) actuating a high speed motor in the handle portion for effecting rotation of the brush head at a selected speed, a worm gear and flex joint assembly coupling the motor to the brush head for effecting rotation thereof; a lithium based DC power source for operation of the motor, actuation being effected using a variable speed power control device for actuating rotation of the brush head in at least two power settings (iii) placing the rotating brush head in contact with at last one of the user's teeth for a selected time;

(iv) removing the head portion from the user's mouth; and (v) disengaging the high speed motor.

19. A method of cleaning a user's teeth using a motorized toothbrush, which comprises the steps of:

(i) actuating a high speed motor in the handle portion of the toothbrush for effecting rotation of a brush head in a head portion of the toothbrush at a selected speed, the toothbrush comprising a housing including the head portion, a handle portion and a neck portion, a least one of the portions being constructed of a polymeric material, a worm gear and flex joint assembly coupling the motor to the brush head for effecting rotation thereof, a lithium based DC power source for operation of the motor, actuation being effected using a variable speed power control device for actuating rotation of the brush head in at least two power settings, the housing being a sealed on-piece unit (ii) inserting the head portion of the toothbrush in the user's mouth, a brush head being rotatably mounted to the head portion and the neck portion having a bend orienting the brush head for engagement of a user's teeth generally at a right angle thereto;

(iii) placing the rotating brush head in contact with at least one of the user's teeth for a selected time;

(iv) disengaging the high speed motor; and (v) removing the brush head from the user's mouth.

20. A motorized toothbrush and stand, in combination, comprising:

a housing including a handle portion, a neck portion and a head portion, at least one of the portions being constructed of a polymeric material, the housing being a sealed one-piece unit;

a brush head rotatably mounted to the head portion, the neck portion having a bend for orienting the brush head for engagement of a user's teeth generally at a right angle thereto;

a variable, high speed motor for effecting rotation of the brush head, a worm gear and flex joint assembly coupling the motor to the brush head for effecting rotation thereof;

a lithium based DC power source for operation of the motor;

a variable speed power control device for actuating rotation of the brush head in at least two power settings; and a support structure for suspending the toothbrush in a generally upright orientation.

21. A motorized toothbrush comprising:

a housing including a handle portion, a neck portion and a head portion, at least one of the portions being constructed of a polymeric material, the housing being a sealed one-piece unit;

a brush head rotatably mounted to the head portion, the neck portion having a bend for orienting the brush head for engagement of a user's teeth generally at a right angle thereto, and further being adjustably flexible for positioning the brush head in a selected orientation relative to the handle portion;

a variable, high speed motor for effecting rotation of the brush head, a worm gear and flex joint assembly coupling the motor to the brush head for effecting rotation thereof;

a lithium based DC power source for operation of the motor; and a variable speed power control device for actuating rotation of the brush head in at least two power setting.

22. A motorized toothbrush, which comprises:

a housing including a handle portion, a neck portion and a head portion, at least one of the portions being constructed of a polymeric material, the housing being a sealed one-piece unit;

a brush head rotatably and detachably mounted to the head portion, the neck portion having a bend for orienting the brush head for engagement of a user's teeth generally at a right angle thereto, and further being adjustably flexible for position the brush head in a selected orientation relative to the handle portion;

a variable, high speed motor for effecting rotation of the brush head, a worm gear and flex joint assembly coupling the motor to the brush head for effecting rotation thereof;

a lithium based DC power source for operation of the motor; and a variable speed power control device for actuating rotation of the brush head in at least two power setting.

23. A motorized toothbrush assembly which comprises a brush head rotatably mounted to a head portion of the assembly, a variable, high speed motor for effecting rotation of the brush head, a lithium based DC power source for operation of the motor, and a variable power control device for actuating rotation of the brush head, the assembly forming a sealed one-piece unit.

24. The toothbrush assembly set forth in claim 23 wherein the power source is about a 9 volt lithium alkaline battery.

25. The toothbrush assembly set forth in claim 23 wherein the brush head is cone-shaped.

26. The motorized toothbrush set forth in claim 23 wherein the brush head is flat.

27. A motorized toothbrush assembly comprising a brush head rotatably and detachably mounted to a head portion of the assembly, a variable, high speed motor effecting rotation of the brush head, a lithium based DC power source for operation of the motor, and a variable speed power control device for actuating rotation of the brush head, the assembly forming a sealed one-piece unit.

* * * * *